United States Patent [19]

Ryan et al.

[11] Patent Number: 4,854,182

[45] Date of Patent: Aug. 8, 1989

[54] ALIQUOTING OF SERIAL LIQUID SAMPLES

[76] Inventors: Will G. Ryan, 906 South Laflin, Chicago, Ill. 60607; Norman E. Bullock, 320 South Home Ave., Oak Park, Ill. 60302

[21] Appl. No.: 148,927

[22] Filed: Jan. 27, 1988

[51] Int. Cl.$^4$ ............................ G01N 1/28; G01N 1/18
[52] U.S. Cl. ................................ 73/864.64; 73/864.91; 73/863; 422/102; 422/103
[58] Field of Search ............ 73/864.63, 864.64, 864.51, 73/864.91, 863; 422/102, 103; 128/760, 762

[56] References Cited

U.S. PATENT DOCUMENTS

| | | | |
|---|---|---|---|
| 2,667,075 | 1/1954 | Blum | 73/864.63 |
| 3,024,660 | 3/1962 | Tothill | 73/864.64 X |
| 3,405,706 | 10/1968 | Cinqualbre | 128/762 |
| 3,545,932 | 12/1970 | Gilford | 73/864.91 X |
| 3,561,427 | 2/1971 | Profy | 128/762 |
| 3,595,086 | 7/1971 | Bonnet et al. | 73/864.91 X |
| 3,730,352 | 5/1973 | Cohen et al. | 422/102 X |
| 3,785,928 | 1/1974 | Kessler | 422/102 X |
| 3,963,151 | 6/1976 | North, Jr. | 251/9 X |
| 4,004,884 | 1/1977 | Zdrodowski | 422/116 X |
| 4,042,337 | 8/1977 | Griffith | 422/102 |
| 4,126,043 | 11/1978 | Schurmann | 73/863.44 |
| 4,227,413 | 10/1980 | Blum | 73/864.91 X |

FOREIGN PATENT DOCUMENTS

| | | | |
|---|---|---|---|
| 58488 | 9/1891 | Fed. Rep. of Germany ... | 73/864.64 |
| 1302145 | 4/1987 | U.S.S.R. ........................... | 73/864.91 |

*Primary Examiner*—Tom Noland
*Attorney, Agent, or Firm*—Thomas W. Speckman; Douglas H. Pauley

[57] ABSTRACT

An apparatus and process for obtaining an aliquot of serial liquid samples. A measured aliquot of each serial liquid sample is obtained and passed to an aliquot storage chamber with discard of the remainder of each liquid sample. A liquid collection container is provided sufficiently large for the largest single liquid serial sample with a generally vertical aliquot tube forming at least one aliquot measurement chamber, each aliquot measurement chamber having a cross-sectional area in the same relation to the cross-sectional area of the liquid collection chamber as the quantity of each aliquot is desired to bear to the liquid samples and having a bottom in the same horizontal plane as the bottom of the liquid collection container. The apparatus and process is operated by an aliquot valve which in a first position places each aliquot measurement chamber in communication only with the liquid collection chamber and when in a second position, places each aliquot measurement chamber in communication only with a corresponding aliquot storage chamber.

17 Claims, 3 Drawing Sheets

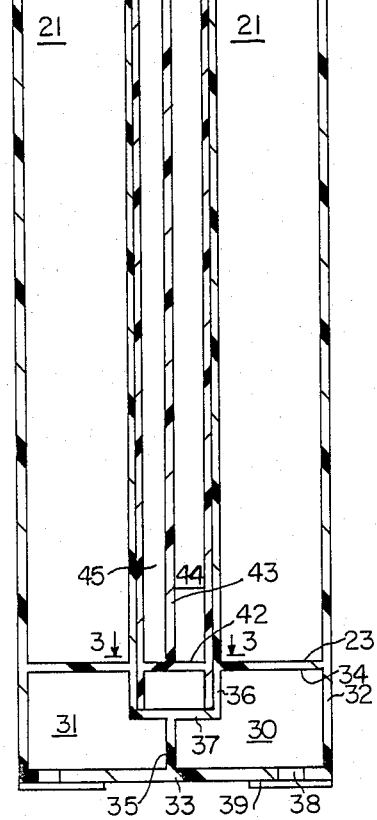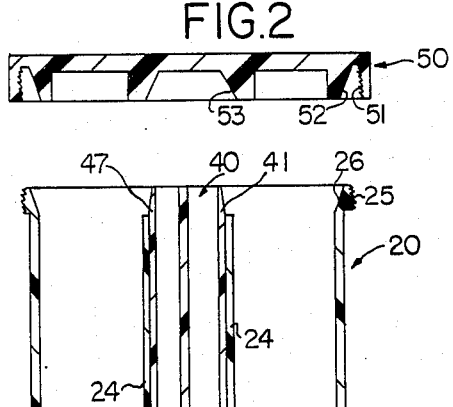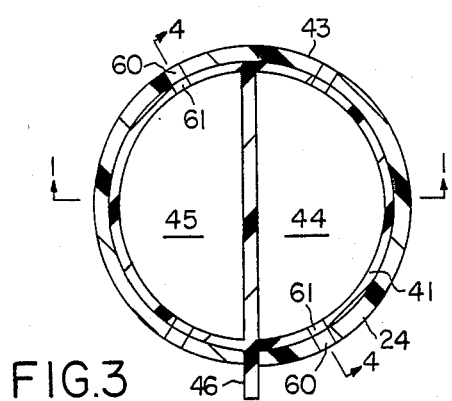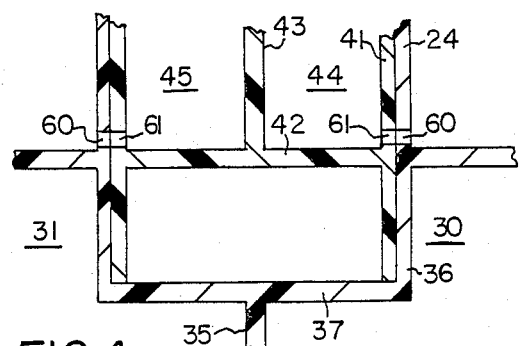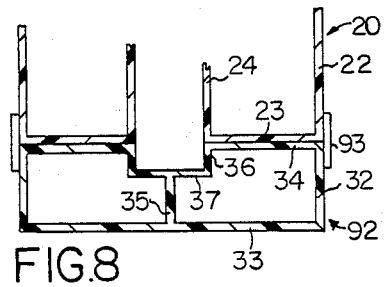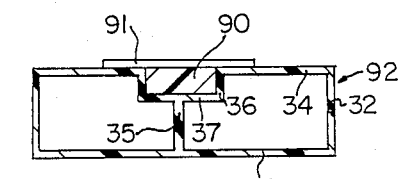

ALIQUOTING OF SERIAL LIQUID SAMPLES

BACKGROUND OF THE INVENTION

1. Field of the Invention

This invention relates to an apparatus and process for obtaining an aliquot of serial liquid samples. Aliquoting of serial liquid samples is desired for many testing routines to provide a mixed fraction of each of a series of samples for a single test routine.

2. Description of the Prior Art

It is frequently desirable for plant quality control or for other testing procedures to obtain a single fractional amount of a series of liquid samples. For example, the laboratory analysis of urine specimens is often a standard procedure in the diagnosis and treatment of various human diseases and ailments, as well as to determine the overall well-being of human bodily functions or the determination of improper functioning of one or more of the processes of the body, organs, glands or systems. The collection and analysis of urine specimens is practiced universally throughout the health delivery industry. While the medical profession has developed and adopted a variety of sophisticated methods and test procedures in the analysis and reporting of data of urine specimens, the routine collection methods have not improved. Many medical analyses require the patient to collect all urine excreted during a 24-hour period. The present method of such collection requires collecting each sample in a container and then transferring each sample to a sufficiently large container to accommodate the 24-hour series of samples or directly adding each sample to the large container. Therefore, the large container must be maintained in proximity to the person being sampled for the entire 24-hour period which is often inconvenient since 24-hour urine samples are frequently needed from active persons engaging in normal activities. To say the least, this method of sample collection of serial samples is inconvenient for the patient throughout the 24-hour day. Frequently, hydrochloric acid or other preservative must be used in connection with maintaining the samples over the 24-hour period and the patient must be cautioned about touching the liquid preservative. In other instances, the samples must be kept cool to prevent growth of bacteria and the patient may be required to refrigerate all of the samples collected over the 24-hour period. The large container must then be returned to the doctor's office, hospital or other sampling center, where laboratory tests are conducted. Normally, the laboratory tests require only about 1 to about 3 percent of the total collection volume. These small amounts are measured and removed from the large serial collection volume and the remainder of the collection volume is then discarded.

A further problem with current liquid sampling techniques as described above has been that in practice, more than one specimen is often required of a patient, and frequently the different samples are required to be subjected to different or no preservatives. In these cases, it is the present practice to perform sequential sampling, that is repeat the process, which has the disadvantage that the second tests are performed on samples which may be very different from the first tests due to various bodily functions and thus the test results are not validly comparable.

SUMMARY OF THE INVENTION

It is an object of this invention to overcome many of the above disadvantages of serial liquid sampling.

It is an object of this invention to provide aliquoting of each serial liquid sample at the time it is taken, storage of only the aliquot amount, and discard of the remainder of each serial liquid sample, thereby providing much smaller and more convenient sampling containers.

It is another object of this invention to provide a plurality of aliquot amounts obtained from a single series of liquid samples.

It is still a further object of this invention to provide a plurality of aliquot amount storage chambers which may contain different preservatives or no preservative for the different aliquot amount storage chambers, corresponding to testing procedures.

It is yet another object of this invention to provide an effective antibiotic preservative to an aliquot storage chamber to effectively preserve the aliquot amount in the aliquot storage chamber.

The above objects of this invention and further features which will become apparent are achieved by a liquid aliquoting apparatus for obtaining an aliquot of a series of liquid samples, the apparatus comprising: a liquid collection container forming a liquid collection chamber; an aliquot container forming at least one aliquot storage chamber below the liquid collection chamber; a generally vertical aliquot tube forming at least one aliquot measurement chamber, each aliquot measurement chamber having a cross-sectional area in the same relation to the cross-sectional area of the liquid collection chamber as the quantity of each aliquot is desired to bear to the liquid samples and having a bottom in the same horizontal plane as the bottom of the liquid collection container, and aliquot valve means which in a first position places each aliquot measurement chamber in communication only with the liquid collection chamber and when in a second position places each aliquot measurement chamber in communication only with a corresponding aliquot storage chamber.

In preferred embodiments, 2 to about 4 aliquot measurement chambers are provided with a corresponding number of aliquot storage chambers.

Preferred embodiments include the liquid collection chamber and the aliquot storage chambers in a single partitioned outer container having the generally vertically aliquot tube in a central position extending to the top of the liquid collection container, thereby forming an annular liquid collection chamber.

Preferred embodiments incorporate the aliquot valve means as a series of passageways in the lower portion of the aliquot tube and a liquid collection chamber inner side wall whereby rotation of the aliquot tube effects the necessary liquid communication as desired for first passing the liquid from the liquid collection chamber to only the aliquot measurement chamber and then passing the liquid from each aliquot measurement chamber to a corresponding aliquot storage chamber. Other preferred embodiments effect the same liquid communication relationships by a vertical movement, or "push-pull" action, of the aliquot valve in respect to the collection and storage chamber inner side walls.

The process for collecting at least one aliquot of serial liquid samples according to this invention includes the steps sequentially comprising: adding the first of a series of liquid samples to a liquid collection chamber; placing the liquid collection chamber in liquid communication only with at least one generally vertical aliquot measurement chamber, each aliquot measurement chamber having a cross-sectional area in the same relation to the cross-sectional area of the liquid collection chamber as the quantity of the aliquot is desired to bear to the liquid samples, and a bottom in the same horizontal plane as a bottom of the liquid collection chamber; passing liquid from the liquid collection chamber into the aliquot measurement chamber until the liquid level in the aliquot measurement chamber is equal to the liquid level in the liquid collection chamber forming an aliquot amount in the aliquot measurement chamber; placing the aliquot measurement chamber in liquid communication with a corresponding aliquot storage chamber; passing the aliquot amount from the aliquot measurement chamber to a corresponding aliquot storage chamber; closing the aliquot storage chamber from communication with the aliquot measurement chamber; discharging the remainder of the serial liquid sample from the liquid collection chamber; and repeating the process for the desired number of serial liquid samples.

It is seen that the apparatus and process for aliquoting of serial liquid samples provided by this invention is suitable for obtaining desired fractions of serial liquid samples while storing only the measured fraction amount of each serial sample and discharging the remainder of each sample, and then repeating the process with the next of the series of liquid samples. The successively obtained aliquot measured amounts in the aliquot storage chamber may bear the same fractional relation to the total volume of the series of samples as each aliquot bears to each liquid sample. Therefore, a collection of aliquoted amounts of a large volume from a series of liquid samples may be obtained using an apparatus of sufficient size to measure an aliquot of only the largest volume of the series and of sufficient size to store the total measured aliquot amount of the series. This provides a much smaller apparatus than currently used and further requires preservation of a much smaller volume in the aliquot storage chamber rendering more effective and use of different methods of preservation than current sampling methods.

It can be readily appreciated that the apparatus and process for obtaining liquid aliquots of a series of liquid samples according to this invention may be readily applied not only to medical applications, but to a wide variety of chemical plant, water, or other liquid testing requirements where a series of liquid samples must be taken for testing.

BRIEF DESCRIPTION OF THE DRAWING

The above and further objects and advantages of this invention will be apparent from the detailed description of further embodiments and by reference to the drawings wherein:

FIG. 1 is a side sectional view of a liquid aliquoting apparatus according to this invention along the section shown as 1—1 in FIG. 3;

FIG. 2 is a side sectional view of the cap for an apparatus as shown in FIG. 1;

FIG. 3 is a top sectional view along the section shown in FIG. 1 as 3—3 showing an aliquot valve means in a first position placing each aliquot measurement chamber in communication only with the liquid collection chamber of the central portion of the apparatus shown in FIG. 1;

FIG. 4 is a partial side sectional view along the section 4—4 shown in FIG. 3;

FIG. 8 is a partial side sectional view of an embodiment of this invention having a removable aliquot storage container;

FIG. 9 is a side sectional view of the aliquot storage container shown in FIG. 8 in a removed position;

DESCRIPTION OF PREFERRED EMBODIMENTS

Figure 5:
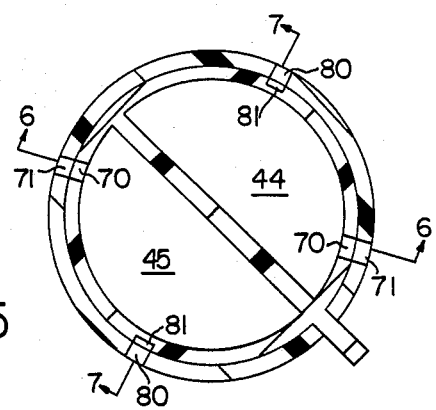
FIG. 5 is a top sectional view corresponding to FIG. 3 showing the aliquot valve means in a second position placing each aliquot measurement chamber in communication only with a corresponding aliquot storage chamber.

Referring to FIG. 1, a single liquid collection container 20 having outer side wall 22 and bottom side wall 23 together with inner side wall 24 forms annular liquid collection chamber 21. Aliquot storage chambers 30 and 31 are below liquid collection chamber 21 and defined by side walls 32, bottom wall 33, top wall 34, partition wall 35, valve well side walls 36 and valve well bottom wall 37. As shown in FIG. 1, the aliquot storage chambers are within a container contiguous with liquid collection container 20. Round tubular-shaped liquid collection chamber inner side wall 24, while shown in FIG. 1 on a central axis of liquid collection container 20 need not be on such a central axis but may even be adjacent an outer side wall 22. The only restriction in location of the tube formed by inner side wall 24 is access to the desired plurality of aliquot storage chambers below the liquid collection container by the valve means to be described.

Aliquot tube 40 is formed with side walls 41 to fit snugly within the tubular structure formed by liquid collection container inner side wall 24 and bottom wall 42 located to have its top surface in approximately the same plane as bottom wall 23 of liquid collection chamber 21. As shown in FIGS. 1-7, aliquot tube 40 is divided into two aliquot measurement chambers 44 and 45 by partition wall 43. The inner volume of aliquot tube 40 may be divided into any desired number of aliquot measurement chambers to provide the desired number of separate measured aliquot fractions of the series of liquid samples. Each aliquot measurement chamber, such as 44 and 45, should have a cross-sectional area in the same relation to the cross-sectional area of the liquid collection chamber as the quantity of each aliquot amount is desired to bear to the liquid samples in instances where the bottom wall 42 is in approximately the same plane as bottom wall 23. Generally, the cross-sectional area of each aliquot measurement chamber is about 1 to about 10 percent the cross-sectional area of the liquid collection chamber, and in medical applications frequently about 1 to about 3 percent. The tube formed by liquid collection chamber inner side wall 24 and the cross-sectional area formed by the inside dimensions of aliquot tube 40 are sized to provide the desired number and size of aliquot amounts of the series of liquid samples. The aliquot measurement chambers within a single aliquot tube may be of the same or of different cross-sectional areas to provide the same or different total aliquot amounts for desired testing. Aliquot tube 40 may be held in desired vertical position in tubular structure 24 by any suitable means, such as "O" rings or detents and grooves or other positioning means known to the art. Likewise, liquid passage between aliquot tube 40 and tubular structure 24 may be restricted by any suitable means known to the art, such as "O" rings, grease seals, and the like.

While the aliquot measurement chambers will generally have constant cross-sectional areas for their collecting length, if it is desired to measure different volume fractions dependent upon the volume of each serial sample, this can be achieved by providing a tapered aliquot measurement chamber having increasing or decreasing cross-sectional area or by curving a constant cross-sectional area tube which may provide greater aliquot fractions at either smaller or larger serial sample volumes. Likewise, the cross-sectional are of the liquid collection chamber may be altered along its length. The basic relationships pointed out above remain between cross-sectional areas of the aliquot measurement chamber and the liquid collection chamber at the same horizontal plane.

Figure 6:
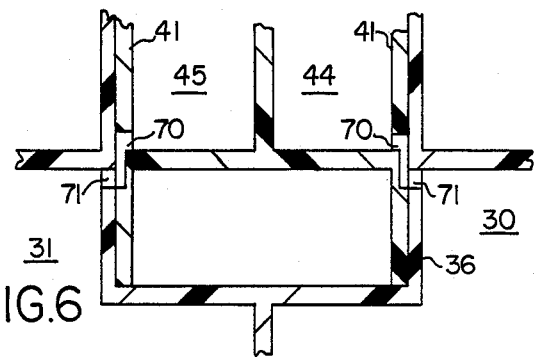
FIG. 6 is a partial side sectional view along the section 6—6 shown in FIG. 5.
Figure 7:
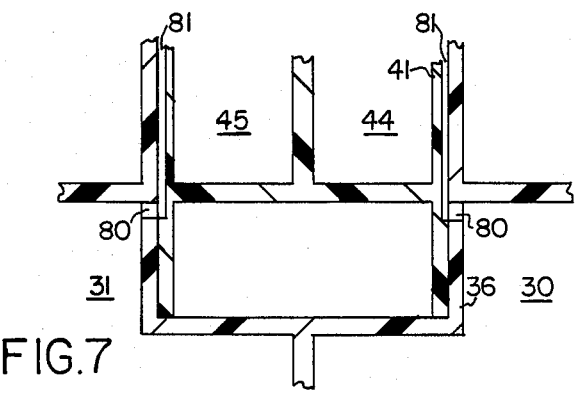
FIG. 7 is a partial side sectional view along the section 7—7 shown in FIG. 5.

In operation, one of the serial liquid samples is added to liquid collection chamber 21. During addition of the serial liquid sample to the liquid collection chamber, or after collection of the serial liquid sample in the liquid collection chamber, the liquid collection chamber is placed in liquid communication with the generally vertical aliquot measurement chambers by rotation of aliquot tube 40 within liquid collection chamber inner side wall 24 by handle 46. As shown in FIGS. 3–7, rotation of aliquot tube 40 within liquid collection chamber inner side wall 24 functions as an aliquot valve as will be explained in more detail. FIGS. 3 and 4 show the aliquot valve in a first position placing each aliquot measurement chamber in communication only with the liquid collection chamber. FIGS. 5–7 show the aliquot valve in a second position placing each aliquot measurement chamber in communication only with a corresponding aliquot storage chambers number 30 and 31. Intermediate positions provide isolation of the aliquot measurement chambers.

The aliquot valve first position as shown in FIGS. 3 and 4 is used in transfer and measurement of an aliquot amount of liquid from the liquid collection chamber 21 to aliquot measurement chambers 44 and 45. As best seen in FIG. 4, aliquot measurement inlet opening 61 in aliquot tube wall 41 is aligned with aliquot measurement inlet opening 60 in liquid collection chamber inner side wall 24. In this position, the liquid will flow from liquid collection chamber 21 to each aliquot measurement chamber 44 and 45 and seek the same levels in the aliquot measurement chambers as in the liquid collection chamber 21, thereby providing a predetermined fraction of the total liquid in liquid collection chamber 21 to the aliquot measurement chambers. In cases where the bottom walls of the aliquot measurement chambers are in approximately the same plane as the bottom wall of the liquid collection chamber, the aliquot fraction amount is directly related to the cross-sectional areas of these chambers. While the aliquot measurement inlet openings 60 and 61 are shown to be adjacent aliquot measurement chamber bottom wall 42 and liquid collection chamber bottom wall 23, it should be readily apparent that these openings may be at any location below the liquid surface of the smallest of the series of liquid samples.

The aliquot valve second position as shown in FIGS. 5–7, is used in transfer of the measured aliquot amount of liquid from the aliquot measurement chambers 44 and 45 to corresponding aliquot storage chambers 30 and 31. As best seen in FIG. 6, aliquot outlet opening 70 in aliquot measurement chamber side wall 41 is aligned with aliquot outlet opening 71 in valve well side wall 36. In this position, the measured aliquot amount will flow from each aliquot measurement chamber to a corresponding aliquot storage chamber, such as from aliquot measurement chamber 44 to aliquot storage chamber 30. To facilitate the liquid flow to the aliquot storage chambers, it is preferred that each aliquot storage chamber be provided with at least one air vent to allow escape of the air with the concomitant liquid filling. One manner of providing such an air vent is through the aliquot valve as shown in FIG. 7. Air outlet opening 80 passes through valve well side wall 36 in communication with air outlet passage 81 in aliquot tube side wall 41 to the top of liquid collection container inner side wall 24 to permit the escape of air from the aliquot storage chambers to the ambient atmosphere.

To assist the user in the proper use of the valve, the aliquot tube 40 to which handle 46 is affixed, may be marked to show the two operating positions of the valve with instructions for each of these operating positions, such as in the first operating position "Fill and Carry Position", and in the second operating position "Sample Transfer Position".

In the above description of the aliquot valve and in the drawings, specific structure has been referred to and it should be readily apparent that these structures may be modified as long as the desired liquid communication and liquid isolation relations are obtained. For example, where reference has been made to single openings, it is readily apparent that multiple openings may be suitable for more rapid operation. Likewise, the positioning of the openings may be varied within limits providing desired liquid communication and isolation.

An important aspect of the invention is in achieving simultaneous multiple measured aliquot amounts from each of a series of liquid samples and transferring the measured aliquot amounts to an aliquot storage chamber allowing disposal of the remainder of the liquid sample from the liquid collection container. This permits use of a small sized liquid collection container and permits measurement and storage of a desired plurality of aliquot amounts, the storage being in separated storage chambers which may be subjected to differing or no preservative or other chemical treatments.

Liquid collection container top 50 is provided for tight closing of liquid collection chamber 21. In one embodiment shown in FIG. 2, liquid collection container top has screw threads 51 engageable with screw threads 25 at the top of liquid collection container outer side wall 20. To further assure tight sealing, sloping surface 52 may be provided to engage receiving surface 26 and sloping surface 53 may be provide to engage receiving surface 47. It is readily apparent that snap-on caps or any other suitable firmly closing top may be used to close liquid collection container 20.

As shown in FIG. 1, it is desirable to provide aliquot storage chamber access hole 38 to each aliquot storage chamber providing ready access to the individual aliquot storage chamber for removal of the aliquot amount, for further aliquoting of the already measured aliquot amount, for adding chemicals to the aliquot storage chamber for testing or preservation purposes, and the like. This may be achieved by providing any suitable tightly closing cover 39 over aliquot storage chamber access 38, shown in FIG. 1 to be a pressure sensitive tape.

In other embodiments of this invention, the aliquot storage chamber container may be separable from the upper liquid collection container 20 to provide a smaller package, for example, for shipping to an anlysis center. In such cases, the top portion or liquid collection container 20 may be discarded or reused on other lower portions or aliquot storage chamber containers. FIG. 8 shows one embodiment providing aliquot container 92 which is removable from liquid collection container 20. The aliquot container and aliquot storage chambers in this embodiment are the same as described with respect to the previous figures except that liquid collection container 20 is provided with a bottom wall 23 separate from top wall 34 of the aliquot storage chambers. Assurance of desired rotary alignment of removable aliquot container 92 with liquid collection container 20 to provide desired operation of the aliquot valve as described above, may be obtained by any suitable means known to the art, such as detents and dimples in the opposing adjacent surfaces of the liquid collection chamber bottom wall and aliquot storage chamber top wall, or by any opposing interlocking means on the outside of side walls 22 and 32. Likewise, any suitable means for tightly fastening removable aliquot container 92 to the bottom of liquid collection container 20 may be used, such as pressure sensitive tape 93 or any clamping or interlocking structure on the exterior of these side walls. FIG. 9 shows removable aliquot container 92 in the removed position with aliquot storage chamber closing plug 90 maintained in position by pressure sensitive sealing tape 91. In such condition, a small sized container may hold measured aliquots of a series of liquid samples and be conveniently transported.

Figure 10:
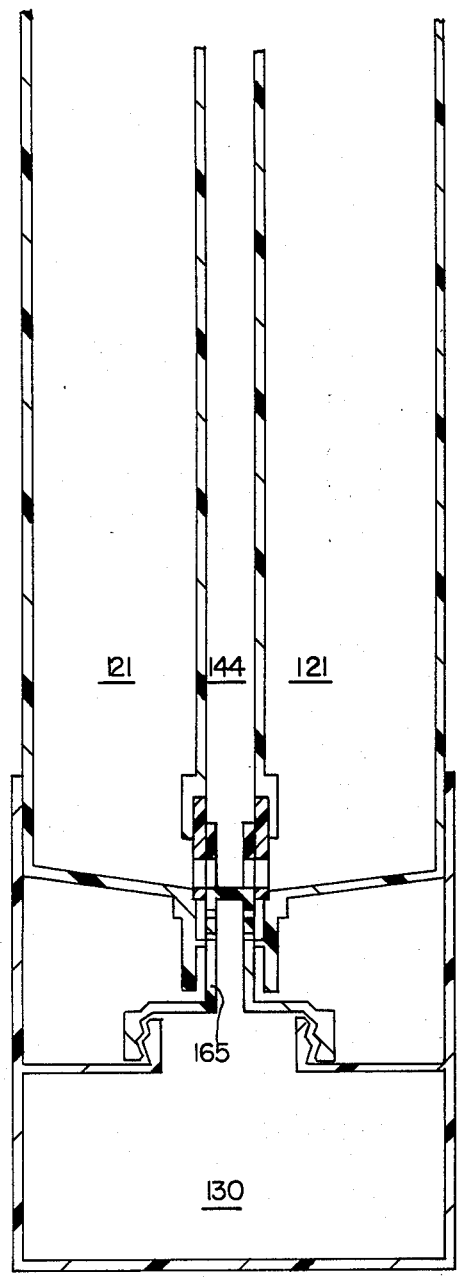
FIG. 10 is a side sectional view of another liquid aliquoting apparatus of this invention.
Figure 11:
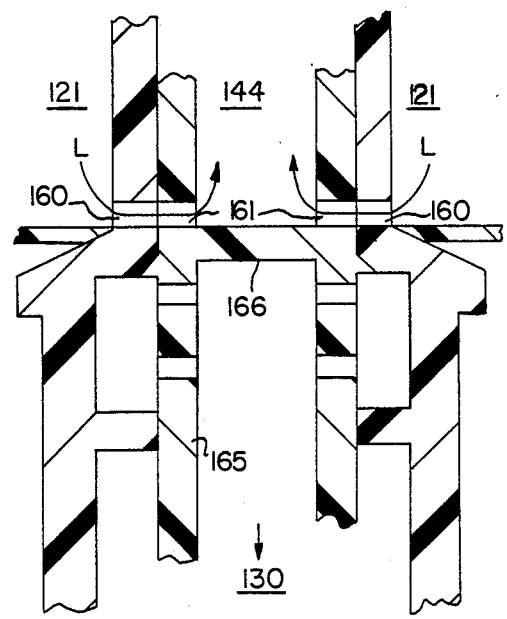
FIG. 11 is a side sectional view showing an aliquot valve means in a first position placing the aliquot measurement chamber in communication only with the liquid collection chamber of the apparatus shown in FIG. 10.
Figure 12:
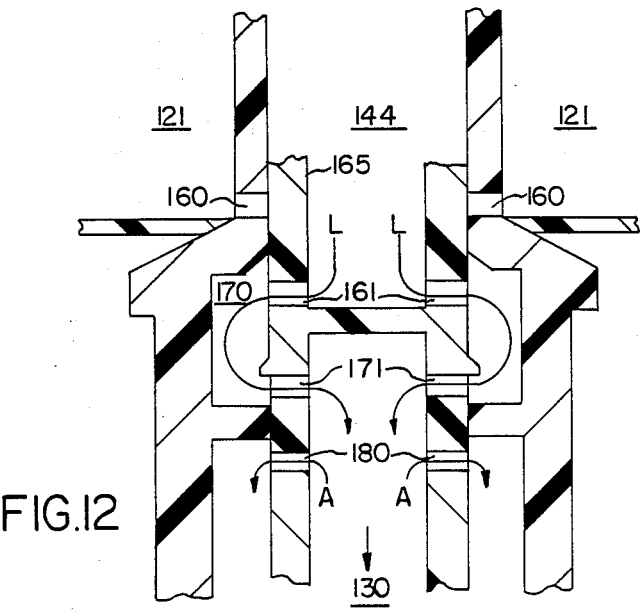
FIG. 12 is a side sectional view corresponding to FIG. 11 showing the aliquot valve means in a second position placing the aliquot measurement chamber in communication only with the aliquot storage chamber.

FIGS. 10 through 12 show another apparatus for aliquoting of serial liquid samples in accordance with this invention. The overall function of the apparatus and method of aliquoting is the same as described above except that a vertically moving "push-pull" valve means is used to provide the necessary liquid communication as described above. FIG. 10 shows the general relation of the push-pull valve means in respect to liquid collection chamber 121, aliquot measurement chamber 144, and aliquot storage chamber 140. FIG. 11 shows push-pull valve 165 as a tubular structure having partition 166 in approximately the same plane as the bottom wall of liquid collection chamber 121 and shows the valve to be in a first position placing aliquot measurement chamber 144 in communication only with liquid collection chamber 121 through openings 160 and 161. In this first position, the liquid passes from liquid collection chamber 121 to aliquot measurement chamber 144, as shown by arrows indicated by "L", and fills to the same level as in liquid collection chamber 121, as described above. Following measurement of the aliquot sample in aliquot measurement chamber 144, valve 165 is depressed, by any suitable means, to the second position shown in FIG. 12. In the second position, aliquot measurement chamber 144 is in liquid communication with aliquot storage chamber 130 through openings 161, chamber 170, and openings 171, with the liquid flowing from aliquot measurement chamber 144 to aliquot storage chamber 130 in the manner shown by arrows labeled "L". To facilitate flow of the measured aliquot amount to aliquot storage chamber 130, air outlets 180 are provided to allow the escape of air to the exterior ambient atmosphere by any suitable means which, upon movement of valve 165 to the first position, closes such air vents. As described more fully above, multiple aliquot measurement chambers with corresponding aliquot storage chambers may be used with modifications to the structure which are readily apparent to one skilled in the art upon reading of this disclosure, or by providing multiple aliquot tubes, valves and collection containers, usually from two to about four.

It is apparent that the apparatus of this invention may be constructed in many sizes to accommodate a wide range of volumes of serial samples and aliquot measured amounts, as well as constructed of a wide variety of materials, such as polyethylene, polystyrene, polypropylene, and the like. It is also readily apparent that different parts of the apparatus may be constructed of different materials having quite different properties, such as construction of aliquot storage chambers from a flexible material with construction of sample collection chambers and valve components of a rigid material.

This invention provides the means for different treatments of a plurality of measured aliquot amounts of serial samples in the aliquot storage chambers. A different chemical or other preservative may be added to each of the plurality of aliquot storage chambers. The preservative treatment is more effective in the apparatus of this invention since only a small portion, in the order of a few percent, of the entire serial sample must be so treated. This, further, makes feasible different preservative methods than currently practiced with large sample volumes. For example, an antibiotic agent, such as Gentamicin sulfate, may be added to at least one of the aliquot storage chambers in an amount sufficient to prevent undesired bioactivity in the aliquot storage amount in that aliquot storage chamber. This is especially important with respect to biological sampling, particularly urine sampling, since the appropriate antibiotic will no contaminate the sample nor alter the test results. Even when conventional acid preservatives are utilized, the preservation of only a small volume of the total serial sample allows different techniques to be used than the current provision of a quantity of liquid in the bottom of the sample container. For example, a sponge saturated with preservative acid, avoiding liquid acid, may be placed in the aliquot storage chamber which cannot be accessed by a patient.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A liquid aliquoting apparatus for obtaining an aliquot of a series of liquid samples comprising: a liquid collection container forming a liquid collection chamber; an aliquot container forming at least one aliquot storage chamber vertically below said liquid collection chamber; a generally vertical aliquot tube forming at least one aliquot measurement chamber, each said aliquot measurement chamber having a cross-sectional area in the same relation to the cross-sectional area of said liquid collection chamber as the quantity of said aliquot is desired to bear to said liquid samples and a bottom in approximately the same horizontal plane as a bottom of said liquid collection container; and aliquot valve means in a first position placing each said aliquot measurement chamber in communication only with said liquid collection chamber and in a second position placing each said aliquot measurement chamber in communication only with each corresponding said aliquot storage chamber.

2. A liquid aliquoting apparatus according to claim 1 wherein said liquid collection container has a central vertical tube which provides said liquid collection chamber with an annular shape, and said aliquot tube is positioned within said central vertical tube, said aliquot tube extends into a well in the upper portion of said aliquot storage chambers, and said aliquot tube is rotatable for predetermined arcuate portions.

3. A liquid aliquoting apparatus according to claim 2 wherein said valve means comprises alignable openings in said aliquot tube and said central vertical tube in said first position and comprises alignable openings in said aliquot tube and said well into said corresponding aliquot storage container in a second position.

4. A liquid aliquoting apparatus according to claim 3 wherein said aliquot tube comprises 2 to 4 aliquot measurement chambers and said aliquot container comprises a corresponding 2 to 4 aliquot storage chambers.

5. A liquid aliquoting apparatus according to claim 1 wherein said aliquot tube comprises 2 to 4 aliquot measurement chambers and said aliquot container comprises a corresponding 2 to 4 aliquot storage chambers.

6. A liquid aliquoting apparatus according to claim 1 wherein said cross-sectional area of each said aliquot measurement chamber is about 1 to about 10 percent the cross-sectional area of said liquid collection chamber.

7. A liquid aliquoting apparatus according to claim 1 wherein said cross-sectional area of each said aliquot measurement chamber is about 1 to about 3 percent the cross-sectional area of said liquid collection chamber.

8. A liquid aliquoting apparatus according to claim 1 wherein said valve means comprises a tubular structure having a partition providing said bottom of each said aliquot measurement chamber and openings alignable to provide said communication in said first and second positions.

9. In a liquid aliquoting apparatus of claim 1 wherein said aliquot tube is central within said liquid collection container and said aliquot valve means comprises a tubular structure having one end extending into each said aliquot measurement chamber and having a partition serving as said bottom of each said aliquot measurement chamber, said tubular structure having at least one through hole on each side of said partition, said tubular structure axially movable for predetermined distance to effect said first position and said second position.

10. In a liquid aliquoting apparatus for obtaining an aliquot of a series of liquid samples; a liquid collection container forming a liquid collection chamber and a generally vertical aliquot tube forming a plurality of aliquot measurement chambers, each said aliquot measurement chamber being in liquid communication with said liquid collection chamber, having a cross-sectional area in the same relation to the cross-sectional area of said liquid collection chamber as the quantity of said aliquot is desired to bear to said liquid samples, and a bottom in approximately the same horizontal plane as a bottom of said liquid collection container whereby a plurality of aliquot measured amounts of each said liquid sample is obtained in said aliquot measurement chambers.

11. In a liquid aliquoting apparatus of claim 10 wherein said aliquot tube comprises 2 to 4 aliquot measurement chambers.

12. In a liquid aliquoting apparatus of claim 10 wherein said cross-sectional area of each said aliquot measurement chamber is about 1 to about 10 percent the cross-sectional area of said liquid collection chamber.

13. In a liquid aliquoting apparatus of claim 10 wherein said cross-sectional area of each said aliquot measurement chamber is about 1 to about 3 percent the cross-sectional area of said liquid collection chamber.

14. In a liquid aliquoting apparatus for obtaining an aliquot of a series of liquid samples; an aliquot tube having at least one inlet opening and at least one outlet opening which in a first position of said aliquot tube places at least one aliquot measurement chamber in communication only with a liquid collection chamber in which said series of liquid sample are collected, there being a corresponding aliquot storage chamber for each aliquot measurement chamber such that said aliquot tube in a second position thereof places each aliquot measurement chamber in communication only with its corresponding aliquot storage chamber, and in a third position thereof said aliquot tube places each aliquot measurement chamber in isolation with respect to its corresponding aliquot storage chamber.

15. In a liquid aliquoting apparatus of claim 14 wherein in said second position each aliquot storage chamber is placed in communication with the ambient atmosphere for escapement of air.

16. In a liquid aliquoting apparatus for obtaining an aliquot of a series of liquid samples; an aliquot valve means which in a first position places at least one aliquot measurement chamber in communication only with a liquid collection chamber in which said series of liquid samples are collected, in a second position places said at least one aliquot measurement chamber correspondingly in communication only with at least one corresponding aliquot storage chamber, and in a third position places said at least one aliquot measurement chamber correspondingly in isolation with respect to said at least one corresponding aliquot storage chamber, and an aliquot tube forming said at least one aliquot measurement chamber is rotatable with respect to an aliquot container forming said at least one corresponding aliquot storage chamber to effect said valve positions for said communication and isolation.

17. In a liquid aliquoting apparatus for obtaining an aliquot of a series of liquid samples; an aliquot valve means which in a first position places at least one aliquot measurement chamber in communication only with a liquid collection chamber in which said series of liquid samples are collected, in a second position places said a least one aliquot measurement chamber correspondingly in communication only with at least one corresponding aliquot storage chamber, and in a third position places said at least one aliquot measurement chamber correspondingly in isolation with respect to said at least one corresponding aliquot storage chamber, and an aliquot tube forming said at least one aliquot measurement chamber and which is moveable axially with respect to an aliquot container forming said at least one corresponding aliquot storage chamber to effect said valve positions for said communication and isolation.

* * * * *